US007699805B2

(12) United States Patent
Mulier et al.

(10) Patent No.: US 7,699,805 B2
(45) Date of Patent: Apr. 20, 2010

(54) HELICAL COIL APPARATUS FOR ABLATION OF TISSUE

(75) Inventors: Peter M. J. Mulier, Stillwater, MN (US); Michael F. Hoey, Shoreview, MN (US); Richard H. Comben, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 31 days.

(21) Appl. No.: 11/998,743

(22) Filed: Nov. 30, 2007

(65) Prior Publication Data

US 2008/0091194 A1   Apr. 17, 2008

Related U.S. Application Data

(63) Continuation of application No. 11/169,275, filed on Jun. 28, 2005, now Pat. No. 7,309,325, which is a continuation of application No. 10/014,388, filed on Oct. 22, 2001, now Pat. No. 6,911,019, which is a continuation of application No. 09/347,752, filed on Jul. 6, 1999, now Pat. No. 6,537,248.

(60) Provisional application No. 60/091,969, filed on Jul. 7, 1998.

(51) Int. Cl.
*A61F 7/12* (2006.01)
(52) U.S. Cl. .................. 604/114; 604/500; 604/22; 606/41; 607/101
(58) Field of Classification Search ............... 604/20, 604/21, 22, 114, 117, 500–510, 118, 272, 604/273; 606/41, 47, 49, 50, 27, 33, 44, 606/42, 46; 607/113, 122, 99, 105, 120, 607/126, 127, 701; 600/374
See application file for complete search history.

(56) References Cited

U.S. PATENT DOCUMENTS

| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Manuel A Mendez
(74) *Attorney, Agent, or Firm*—Mike Jaro; Jeffrey J. Hohenshell

(57) ABSTRACT

A surgical apparatus for delivering a conductive fluid to a target site for subsequent formation of a virtual electrode to ablate bodily tissue at the target site by applying a current to the delivered conductive fluid. The surgical apparatus includes an elongated device forming a helical needle. The helical needle is configured to engage bodily tissue and is hollow for delivering conductive fluid from a fluid source. Finally, the helical needle terminates in a needle tip. In one preferred embodiment, an electrode is associated with the helical needle for applying a current to conductive fluid delivered from the helical needle. During use, following delivery of conductive fluid, the electrode applies a current to the delivered conductive fluid for creating a virtual electrode. The virtual electrode ablates bodily tissue contacted by the conductive fluid.

23 Claims, 4 Drawing Sheets

U.S. PATENT DOCUMENTS

| | | |
|---|---|---|
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,321,931 A | 3/1982 | Hon |
| 4,355,642 A | 10/1982 | Alferness |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,125,928 A | 6/1992 | Parins et al. |
| 5,147,355 A | 9/1992 | Freidman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,421,819 A | 6/1995 | Edwards et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,435,805 A | 7/1995 | Edwards et al. |
| 5,437,651 A | 8/1995 | Todd et al. |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,462,521 A | 10/1995 | Brucker et al. |
| 5,462,545 A | 10/1995 | Wang et al. |
| 5,465,717 A | 11/1995 | Imran et al. |
| 5,469,853 A | 11/1995 | Law et al. |
| 5,470,308 A | 11/1995 | Edwards et al. |
| 5,470,309 A | 11/1995 | Edwards et al. |
| 5,472,876 A | 12/1995 | Fahy |
| 5,478,309 A | 12/1995 | Sweezer et al. |
| 5,478,330 A | 12/1995 | Imran et al. |
| 5,484,400 A | 1/1996 | Edwards et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,542,915 A | 8/1996 | Edwards et al. |
| 5,542,928 A | 8/1996 | Evans et al. |
| 5,545,171 A | 8/1996 | Sharkey et al. |
| 5,545,195 A | 8/1996 | Lennox et al. |
| 5,545,200 A | 8/1996 | West et al. |
| 5,549,661 A | 8/1996 | Kordis et al. |
| 5,554,110 A | 9/1996 | Edwards et al. |
| 5,555,883 A | 9/1996 | Avitall |
| 5,556,377 A | 9/1996 | Rosen et al. |
| 5,558,671 A | 9/1996 | Yates |
| 5,558,673 A | 9/1996 | Edwards et al. |
| 5,560,362 A | 10/1996 | Silwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,589 A | 12/1996 | Edwards et al. |
| 5,582,609 A | 12/1996 | Swanson et al. |

| | | | | | |
|---|---|---|---|---|---|
| 5,584,872 A | 12/1996 | LaFontaine et al. | 5,844,349 A | 12/1998 | Oakley et al. |
| 5,588,432 A | 12/1996 | Crowley | 5,846,187 A | 12/1998 | Wells et al. |
| 5,588,960 A | 12/1996 | Edwards et al. | 5,846,191 A | 12/1998 | Wells et al. |
| 5,590,657 A | 1/1997 | Cain et al. | 5,849,011 A | 12/1998 | Jones et al. |
| 5,591,125 A | 1/1997 | Edwards et al. | 5,849,028 A | 12/1998 | Chen |
| 5,595,183 A | 1/1997 | Swanson et al. | 5,871,481 A | 2/1999 | Kannenberg et al. |
| 5,599,294 A | 2/1997 | Edwards et al. | 5,871,523 A | 2/1999 | Fleischman et al. |
| 5,599,295 A | 2/1997 | Rosen et al. | 5,871,525 A | 2/1999 | Edwards et al. |
| 5,607,389 A | 3/1997 | Edwards et al. | 5,873,845 A | 2/1999 | Cline et al. |
| 5,607,462 A | 3/1997 | Imran | 5,873,877 A | 2/1999 | McGaffigan et al. |
| 5,609,151 A | 3/1997 | Mulier | 5,876,398 A | 3/1999 | Mulier et al. |
| 5,617,854 A | 4/1997 | Munsif | 5,876,399 A | 3/1999 | Chia et al. |
| 5,630,794 A | 5/1997 | Lax et al. | 5,879,295 A | 3/1999 | Li et al. |
| 5,630,837 A | 5/1997 | Crowley | 5,879,296 A | 3/1999 | Ockuly et al. |
| 5,637,090 A | 6/1997 | McGee et al. | 5,881,732 A | 3/1999 | Sung et al. |
| 5,643,197 A | 7/1997 | Brucker et al. | 5,882,346 A | 3/1999 | Pomeranz et al. |
| 5,653,692 A | 8/1997 | Masterson et al. | 5,885,278 A | 3/1999 | Fleischman |
| 5,656,029 A | 8/1997 | Imran et al. | 5,888,198 A | 3/1999 | Eggers et al. |
| 5,658,278 A | 8/1997 | Imran et al. | 5,891,095 A | 4/1999 | Eggers et al. |
| 5,667,488 A | 9/1997 | Lundquist et al. | 5,893,848 A | 4/1999 | Negus et al. |
| 5,671,747 A | 9/1997 | Connor | 5,895,417 A | 4/1999 | Pomeranz et al. |
| 5,672,153 A | 9/1997 | Lax et al. | 5,897,553 A | 4/1999 | Mulier et al. |
| 5,673,695 A | 10/1997 | McGee et al. | 5,897,554 A | 4/1999 | Chia et al. |
| 5,676,662 A | 10/1997 | Fleischhacker et al. | 5,899,898 A | 5/1999 | Arless et al. |
| 5,676,692 A | 10/1997 | Sanghvi et al. | 5,899,899 A | 5/1999 | Arless et al. |
| 5,676,693 A | 10/1997 | LaFontaine | 5,902,289 A | 5/1999 | Swartz et al. |
| 5,678,550 A | 10/1997 | Bassen et al. | 5,902,328 A | 5/1999 | LaFontaine et al. |
| 5,680,860 A | 10/1997 | Imran | 5,904,711 A | 5/1999 | Flom et al. |
| 5,681,277 A | 10/1997 | Edwards et al. | 5,906,580 A | 5/1999 | Kline-Schoder et al. |
| 5,681,278 A | 10/1997 | Igo et al. | 5,906,587 A | 5/1999 | Zimmon |
| 5,681,308 A | 10/1997 | Edwards et al. | 5,906,606 A | 5/1999 | Chee et al. |
| 5,683,366 A | 11/1997 | Eggers et al. | 5,906,613 A | 5/1999 | Mulier et al. |
| 5,687,723 A | 11/1997 | Avitall | 5,908,029 A | 6/1999 | Knudson et al. |
| 5,687,737 A | 11/1997 | Branham et al. | 5,913,854 A | 6/1999 | Maguire et al. |
| 5,688,267 A | 11/1997 | Panescu et al. | 5,916,213 A | 6/1999 | Haissaguerre et al. |
| 5,690,611 A | 11/1997 | Swartz et al. | 5,916,214 A | 6/1999 | Cosio et al. |
| 5,697,281 A | 12/1997 | Eggers et al. | 5,921,924 A | 7/1999 | Avitall |
| 5,697,536 A | 12/1997 | Eggers et al. | 5,921,982 A | 7/1999 | Lesh et al. |
| 5,697,882 A | 12/1997 | Eggers et al. | 5,927,284 A | 7/1999 | Borst et al. |
| 5,697,909 A | 12/1997 | Eggers et al. | 5,928,191 A | 7/1999 | Houser et al. |
| 5,697,925 A | 12/1997 | Taylor | 5,931,810 A | 8/1999 | Grabek |
| 5,697,927 A | 12/1997 | Imran et al. | 5,931,848 A | 8/1999 | Saadat |
| 5,697,928 A | 12/1997 | Walcott et al. | 5,954,661 A | 9/1999 | Greenspon et al. |
| 5,713,942 A | 2/1998 | Stern | 5,957,922 A | 9/1999 | Imran |
| 5,716,389 A | 2/1998 | Walinsky et al. | 5,964,727 A | 10/1999 | Edwards et al. |
| 5,718,241 A | 2/1998 | Ben-Haim et al. | 5,971,980 A | 10/1999 | Sherman |
| 5,718,701 A | 2/1998 | Shai et al. | 5,971,983 A | 10/1999 | Lesh |
| 5,720,718 A | 2/1998 | Rosen et al. | 5,993,447 A | 11/1999 | Blewett et al. |
| 5,720,775 A | 2/1998 | Lanard | 6,007,499 A | 12/1999 | Martin et al. |
| 5,722,402 A | 3/1998 | Swanson et al. | 6,012,457 A | 1/2000 | Lesh |
| 5,725,524 A | 3/1998 | Mulier et al. | 6,016,809 A | 1/2000 | Mulier et al. |
| 5,730,074 A | 3/1998 | Peter | 6,016,811 A | 1/2000 | Knopp et al. |
| 5,730,127 A | 3/1998 | Avitall | 6,022,334 A | 2/2000 | Edwards et al. |
| 5,730,704 A | 3/1998 | Avitall | 6,042,556 A | 3/2000 | Beach et al. |
| 5,733,280 A | 3/1998 | Avitall | 6,063,081 A | 5/2000 | Mulier et al. |
| 5,735,280 A | 4/1998 | Sherman et al. | 6,071,279 A | 6/2000 | Whayne et al. |
| 5,735,290 A | 4/1998 | Sterman et al. | 6,088,894 A | 7/2000 | Oakley |
| 5,749,846 A | 5/1998 | Edwards et al. | 6,096,037 A | 8/2000 | Mulier et al. |
| 5,755,760 A | 5/1998 | Maguire et al. | 6,102,886 A | 8/2000 | Lundquist et al. |
| 5,769,846 A | 6/1998 | Edwards et al. | 6,113,592 A | 9/2000 | Taylor |
| 5,782,828 A | 7/1998 | Chen et al. | 6,117,101 A | 9/2000 | Diederich et al. |
| 5,785,706 A | 7/1998 | Bednarek | 6,120,496 A | 9/2000 | Whayne et al. |
| 5,788,636 A | 8/1998 | Curley | 6,129,726 A | 10/2000 | Edwards et al. |
| 5,792,140 A | 8/1998 | Tu et al. | 6,142,993 A | 11/2000 | Whayne et al. |
| 5,797,960 A | 8/1998 | Stevens et al. | 6,142,994 A | 11/2000 | Swanson et al. |
| 5,800,428 A | 9/1998 | Nelson et al. | 6,152,920 A | 11/2000 | Thompson et al. |
| 5,800,482 A | 9/1998 | Pomeranz et al. | 6,161,543 A | 12/2000 | Cox et al. |
| 5,800,486 A | 9/1998 | Thome et al. | 6,165,174 A | 12/2000 | Jacobs et al. |
| 5,807,395 A | 9/1998 | Mulier et al. | 6,193,714 B1 | 2/2001 | McGaffigan et al. |
| 5,810,802 A | 9/1998 | Panescu et al. | 6,206,847 B1 | 3/2001 | Edwards et al. |
| 5,827,216 A | 10/1998 | Igo et al. | 6,217,528 B1 | 4/2001 | Koblish et al. |
| 5,836,947 A | 11/1998 | Fleischman et al. | 6,217,576 B1 | 4/2001 | Tu et al. |
| 5,840,030 A | 11/1998 | Ferek-Petric et al. | 6,224,592 B1 | 5/2001 | Eggers et al. |

| | | | | | | |
|---|---|---|---|---|---|---|
| 6,231,518 B1 | 5/2001 | Grabek et al. | 6,706,039 B2 | 3/2004 | Mulier | |
| 6,235,024 B1 | 5/2001 | Tu | 6,716,211 B2 | 4/2004 | Mulier | |
| 6,237,605 B1 | 5/2001 | Vaska et al. | 6,730,079 B2 | 5/2004 | Lovewell | |
| 6,238,347 B1 | 5/2001 | Nix et al. | 6,736,810 B2 | 5/2004 | Hoey | |
| 6,238,393 B1 | 5/2001 | Mulier | 6,755,827 B2 | 6/2004 | Mulier | |
| 6,245,061 B1 | 6/2001 | Panescu et al. | 6,764,487 B2 | 7/2004 | Mulier | |
| 6,245,064 B1 | 6/2001 | Lesh et al. | 6,773,433 B2 | 8/2004 | Stewart et al. | |
| 6,245,065 B1 | 6/2001 | Panescu et al. | 6,776,780 B2 | 8/2004 | Mulier | |
| 6,251,092 B1 | 6/2001 | Qin et al. | 6,807,968 B2 | 10/2004 | Francischelli | |
| 6,251,128 B1 | 6/2001 | Knopp et al. | 6,814,712 B1 | 11/2004 | Edwards et al. | |
| 6,270,471 B1 | 8/2001 | Hechel et al. | 6,827,715 B2 | 12/2004 | Francischelli | |
| 6,293,943 B1 | 9/2001 | Panescu et al. | 6,849,073 B2 | 2/2005 | Hoey | |
| 6,296,619 B1 | 10/2001 | Brisken et al. | 6,852,091 B2 | 2/2005 | Edwards et al. | |
| 6,302,880 B1 | 10/2001 | Schaer | 6,855,141 B2 | 2/2005 | Lovewell | |
| 6,311,692 B1 | 11/2001 | Vaska et al. | 6,858,028 B2 | 2/2005 | Mulier | |
| 6,312,383 B1 | 11/2001 | Lizzi et al. | 6,887,238 B2 | 5/2005 | Jahns | |
| 6,314,962 B1 | 11/2001 | Vaska et al. | 6,899,711 B2 | 5/2005 | Stewart et al. | |
| 6,314,963 B1 | 11/2001 | Vaska et al. | 6,911,019 B2 | 6/2005 | Mulier | |
| 6,322,559 B1 | 11/2001 | Daulton et al. | 6,916,318 B2 | 7/2005 | Francischelli | |
| 6,325,797 B1 | 12/2001 | Stewart et al. | 6,936,046 B2 | 8/2005 | Hissong | |
| 6,328,736 B1 | 12/2001 | Mulier | 6,949,097 B2 | 9/2005 | Stewart et al. | |
| 6,332,881 B1 | 12/2001 | Carner et al. | 6,949,098 B2 | 9/2005 | Mulier | |
| 6,358,248 B1 | 3/2002 | Mulier | 6,960,205 B2 | 11/2005 | Jahns | |
| 6,361,531 B1 | 3/2002 | Hissong | 6,962,589 B2 | 11/2005 | Mulier | |
| 6,364,876 B1 | 4/2002 | Erb et al. | 6,989,010 B2 | 1/2006 | Francischelli et al. | |
| 6,368,275 B1 | 4/2002 | Sliwa et al. | 7,029,470 B2 | 4/2006 | Francischelli et al. | |
| 6,371,955 B1 | 4/2002 | Fuimaono et al. | 7,058,447 B2 | 6/2006 | Hill et al. | |
| 6,383,151 B1 | 5/2002 | Diederich et al. | 7,083,620 B2 | 8/2006 | Jahns et al. | |
| 6,385,472 B1 | 5/2002 | Hall et al. | 7,094,235 B2 | 8/2006 | Francischelli | |
| 6,398,792 B1 | 6/2002 | O'Connor | 7,104,989 B2 | 9/2006 | Skarda | |
| 6,409,722 B1 | 6/2002 | Hoey | 7,156,843 B2 | 1/2007 | Skarda | |
| 6,413,254 B1 | 7/2002 | Hissong et al. | 7,156,845 B2 | 1/2007 | Mulier et al. | |
| 6,419,648 B1 | 7/2002 | Vitek et al. | 7,166,105 B2 | 1/2007 | Mulier et al. | |
| 6,419,653 B2 | 7/2002 | Edwards et al. | 7,169,144 B2 | 1/2007 | Hoey et al. | |
| 6,425,867 B1 | 7/2002 | Vaezy et al. | 7,184,829 B2 | 2/2007 | Hill et al. | |
| 6,430,426 B2 | 8/2002 | Avitall | 7,201,731 B1 | 4/2007 | Lundquist et al. | |
| 6,440,130 B1 | 8/2002 | Mulier | 7,225,019 B2 | 5/2007 | Jahns et al. | |
| 6,443,952 B1 | 9/2002 | Mulier | 7,247,155 B2 | 7/2007 | Hoey et al. | |
| 6,447,507 B1 | 9/2002 | Bednarek et al. | 7,250,048 B2 | 7/2007 | Francischelli et al. | |
| 6,461,314 B1 | 10/2002 | Pant et al. | 7,250,051 B2 | 7/2007 | Francischelli | |
| 6,461,356 B1 | 10/2002 | Patterson | 7,261,711 B2 | 8/2007 | Mulier et al. | |
| 6,464,661 B2 | 10/2002 | Edwards et al. | 7,285,119 B2 | 10/2007 | Stewart et al. | |
| 6,464,700 B1 | 10/2002 | Koblish et al. | 7,294,143 B2 | 11/2007 | Francischelli | |
| 6,471,697 B1 | 10/2002 | Lesh | 7,309,325 B2 * | 12/2007 | Mulier et al. | 604/114 |
| 6,471,698 B1 | 10/2002 | Edwards et al. | 7,311,705 B2 | 12/2007 | Sra | |
| 6,474,340 B1 | 11/2002 | Vaska et al. | 7,347,888 B2 | 3/2008 | Francischelli et al. | |
| 6,475,216 B2 | 11/2002 | Mulier | 7,364,578 B2 | 4/2008 | Francischelli et al. | |
| 6,477,396 B1 | 11/2002 | Mest et al. | 7,364,579 B2 | 4/2008 | Mulier et al. | |
| 6,484,727 B1 | 11/2002 | Vaska et al. | 7,367,972 B2 | 5/2008 | Francischelli et al. | |
| 6,488,680 B1 | 12/2002 | Francischelli | 7,422,588 B2 | 9/2008 | Mulier et al. | |
| 6,502,575 B1 | 1/2003 | Jacobs et al. | 7,435,250 B2 | 10/2008 | Francischelli et al. | |
| 6,514,250 B1 | 2/2003 | Jahns et al. | 7,470,272 B2 | 12/2008 | Mulier et al. | |
| 6,527,767 B2 | 3/2003 | Wang et al. | 7,507,235 B2 | 3/2009 | Keogh et al. | |
| 6,537,248 B2 | 3/2003 | Mulier | 7,566,334 B2 | 7/2009 | Christian et al. | |
| 6,551,300 B1 | 4/2003 | McGaffigan | 2003/0045872 A1 | 3/2003 | Jacobs | |
| 6,558,382 B2 | 5/2003 | Jahns | 2003/0144656 A1 | 7/2003 | Ocel | |
| 5,697,536 C1 | 6/2003 | Eggers et al. | 2003/0191462 A1 | 10/2003 | Jacobs | |
| 6,584,360 B2 | 6/2003 | Francischelli | 2003/0216724 A1 | 11/2003 | Jahns | |
| 6,585,732 B2 | 7/2003 | Mulier | 2004/0015106 A1 | 1/2004 | Coleman | |
| 6,605,084 B2 | 8/2003 | Acker et al. | 2004/0015219 A1 | 1/2004 | Francischelli | |
| 6,607,529 B1 | 8/2003 | Jones et al. | 2004/0044340 A1 | 3/2004 | Francischelli | |
| 6,610,054 B1 | 8/2003 | Edwards et al. | 2004/0049179 A1 | 3/2004 | Francischelli | |
| 6,610,055 B1 | 8/2003 | Swanson et al. | 2004/0078069 A1 | 4/2004 | Francischelli | |
| 6,610,060 B2 | 8/2003 | Mulier | 2004/0082948 A1 | 4/2004 | Stewart et al. | |
| 6,613,048 B2 | 9/2003 | Mulier | 2004/0087940 A1 | 5/2004 | Jahns | |
| 6,645,199 B1 | 11/2003 | Jenkins et al. | 2004/0092926 A1 | 5/2004 | Hoey | |
| 6,648,883 B2 | 11/2003 | Francischelli | 2004/0138621 A1 | 7/2004 | Jahns | |
| 6,656,175 B2 | 12/2003 | Francischelli | 2004/0138656 A1 | 7/2004 | Francischelli | |
| 6,663,627 B2 | 12/2003 | Francischelli | 2004/0143260 A1 | 7/2004 | Francischelli | |
| 6,692,450 B1 | 2/2004 | Coleman | 2004/0186465 A1 | 9/2004 | Francischelli | |
| 6,699,240 B2 | 3/2004 | Francischelli | 2004/0215183 A1 | 10/2004 | Hoey | |
| 6,702,811 B2 | 3/2004 | Stewart et al. | 2004/0220560 A1 | 11/2004 | Briscoe | |
| 6,706,038 B2 | 3/2004 | Francischelli | 2004/0236322 A1 | 11/2004 | Mulier | |

| | | |
|---|---|---|
| 2004/0267326 A1 | 12/2004 | Ocel |
| 2005/0010095 A1 | 1/2005 | Stewart et al. |
| 2005/0010203 A1 | 1/2005 | Edwards et al. |
| 2005/0033280 A1 | 2/2005 | Francischelli |
| 2005/0084804 A1 | 4/2005 | Truskett et al. |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0222562 A1 | 10/2005 | Lovewell |
| 2005/0256522 A1 | 11/2005 | Francischelli et al. |
| 2005/0267454 A1 | 12/2005 | Hissong |
| 2006/0009756 A1 | 1/2006 | Francischelli |
| 2006/0009759 A1 | 1/2006 | Chrisitian |
| 2006/0015097 A1 | 1/2006 | Mulier et al. |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J of Thorac Cardiovasc Surg*, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8½ Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

* cited by examiner

HELICAL COIL APPARATUS FOR ABLATION OF TISSUE

CROSS REFERENCE TO RELATED APPLICATIONS

This application is a continuation of U.S. patent application Ser. No. 11/169,275, filed, Jun. 28, 2005 now U.S. Pat. No. 7,309,325, which is a continuation of U.S. patent application Ser. No. 10/014,388, filed, Oct. 22, 2001, now U.S. Pat. No. 6,911,019, which is a continuation of U.S. patent application Ser. No. 09/347,752, filed Jul. 6, 1999, now U.S. Pat. No. 6,537,248, which claims the benefit of U.S. Provisional Application No. 60/091,969, filed on Jul. 7, 1998, which are incorporated by reference herein in their entirety.

FIELD OF THE INVENTION

The present invention relates generally to an apparatus for creating a virtual electrode. More particularly, the present invention relates to an apparatus for the creation of a virtual electrode that is useful for the ablation of soft tissue and neoplasms.

BACKGROUND OF THE PRESENT INVENTION

The utilization of an electric current to produce an ameliorative effect on a bodily tissue has a long history, reportedly extending back to the ancient Greeks. The effects on bodily tissue from an applied electric current, and thus the dividing line between harmful and curative effects, will vary depending upon the voltage levels, current levels, the length of time the current is applied, and the tissue involved. One such effect resulting from the passage of an electric current through tissue is heat generation.

Body tissue, like all non-superconducting materials, conducts current with some degree of resistance. This resistance creates localized heating of the tissue through which the current is being conducted. The amount of heat generated will vary with the power P deposited in the tissue, which is a function of the product of the square of the current I and the resistance R of the tissue to the passage of the current through it ($P=I^2R$.).

As current is applied to tissue, then, heat is generated due to the inherent resistance of the tissue. Deleterious effects in the cells making up the tissue begin to occur at about 42° Celsius. As the temperature of the tissue increases due to heat generated by the tissue's resistance, the tissue will undergo profound changes and eventually, as the temperature becomes high enough, that is, generally greater than 45° C., the cells will die. The zone of cell death is known as a lesion and the procedure followed to create the lesion is commonly called an ablation. As the temperature increases beyond cell death temperature, complete disintegration of the cell walls and cells caused by boiling off of the tissue's water can occur. Cell death temperatures can vary somewhat with the type of tissue to which the power is being applied, but generally will begin to occur within the range of 45° to 60° C., though actual cell death of certain tissue cells may occur at a higher temperature.

In recent times, electric current has found advantageous use in surgery, with the development of a variety of surgical instruments for cutting tissue or for coagulating blood. Still more recently, the use of alternating electric current to ablate, that is, kill, various tissues has been explored. Typically, current having a frequency from about 3 kilohertz to about 300 gigahertz, which is generally known as radiofrequency or radiofrequency (RF) current, is used for this procedure. Destruction, that is, killing, of tissue using an RF current is commonly known as radiofrequency ablation. Often radiofrequency ablation is performed as a minimally invasive procedure and is thus known as radiofrequency catheter ablation because the procedure is performed through and with the use of a catheter. By way of example, radiofrequency catheter ablation has been used to ablate cardiac tissue responsible for irregular heart beats or arrythmias.

The prior art applications of current to tissue have typically involved applying the current using a "dry" electrode. That is, a metal electrode is applied to the tissue desired to be affected and a generated electric current is passed through the electrode to the tissue. A commonly known example of an instrument having such an operating characteristic is an electrosurgical instrument known as a "bovie" knife. This instrument includes a cutting/coagulating blade electrically attached to a current generator. The blade is applied to the tissue of a patient and the current passes through the blade into the tissue and through the patient's body to a metal base electrode or ground plate usually placed underneath and in electrical contact with the patient. The base electrode is in turn electrically connected to the current generator so as to provide a complete circuit.

As the current from the bovie knife passes from the blade into the tissue, the resistance provided by the tissue creates heat. In the cutting mode, a sufficient application of power through the bovie knife to the tissue causes the fluid within the cell to turn to steam, creating a sufficient overpressure so as to burst the cell walls. The cells then dry up, desiccate, and carbonize, resulting in localized shrinking and an opening in the tissue. Alternatively, the bovie knife can be applied to bleeding vessels to heat and coagulate the blood flowing therefrom and thus stop the bleeding.

As previously noted, another use for electrical instruments in the treatment of the body is in the ablation of tissue. To expand further on the brief description given earlier of the ablation of cardiac tissue, it has long been known that a certain kind of heart tissue known as sino-atrial and atrio-ventricular nodes spontaneously generate an electrical signal that is propagated throughout the heart along conductive pathways to cause it to beat. Occasionally, certain heart tissue will "misfire," causing the heart to beat irregularly. If the errant electrical pathways can be determined, the tissue pathways can be ablated and the irregular heartbeat remedied. In such a procedure, an electrode is placed via a catheter into contact with the tissue and then current is applied to the tissue via the electrode from a generator of RF current. The applied current will cause the tissue in contact with the electrode to heat. Power will continue to be applied until the tissue reaches a temperature where the heart tissue dies, thereby destroying the errant electrical pathway and the cause of the irregular heartbeat.

Another procedure using RF ablation is transurethral needle ablation, or TUNA, which is used to create a lesion in the prostate gland for the treatment of benign prostatic hypertrophy (BPH) or the enlargement of the prostate gland. In a TUNA procedure, a needle having an exposed conductive tip is inserted into the prostate gland and current is applied to the prostate gland via the needle. As noted previously, the tissue of the prostate gland heats locally surrounding the needle tip as the current passes from the needle to the base electrode. A lesion is created as the tissue heats and the destroyed cells may be reabsorbed by the body, infiltrated with scar tissue, or just become non-functional.

While there are advantages and uses for such "dry" electrode instruments, there are also several notable disadvantages. One of these disadvantages is that during a procedure, coagulum—dried blood cells and tissue cells—will form on the electrode engaging the tissue. Coagulum acts as an insulator and effectively functions to prevent current transfer from the blade to the tissue. This coagulum "insulation" can be overcome with more voltage so as to keep the current flowing, but only at the risk of arcing and injuring the patient. Thus, during surgery when the tissue is cut with an electrosurgical scalpel, a build-up of coagulated blood and desiccated tissue will occur on the blade, requiring the blade to be cleaned before further use. Typically, cleaning an electrode/scalpel used in this manner will involve simply scraping the dried tissue from the electrode/scalpel by rubbing the scalpel across an abrasive pad to remove the coagulum. This is a tedious procedure for the surgeon and the operating staff since it requires the "real" work of the surgery to be discontinued while the cleaning operation occurs. This procedure can be avoided with the use of specially coated blades that resist the build up of coagulum. Such specialty blades are costly, however.

A second disadvantage of the dry electrode approach is that the electrical heating of the tissue creates smoke that is now known to include cancer-causing agents. Thus, preferred uses of such equipment will include appropriate ventilation systems, which can themselves become quite elaborate and quite expensive.

A further, and perhaps the most significant, disadvantage of dry electrode electrosurgical tools is revealed during cardiac ablation procedures. During such a procedure, an electrode that is otherwise insulated but having an exposed, current carrying tip is inserted into the heart chamber and brought into contact with the inner or endocardial side of the heart wall where the ablation is to occur. The current is initiated and passes from the current generator to the needle tip electrode and from there into the tissue so that a lesion is created. Typically, however, the lesion created by a single insertion is insufficient to cure the irregular heartbeat because the lesion created is of an insufficient size to destroy the errant electrical pathway. Thus, multiple needle insertions and multiple current applications are almost always required to ablate the errant cardiac pathway, prolonging the surgery and thus increasing the potential risk to the patient.

This foregoing problem is also present in TUNA procedures, which similarly require multiple insertions of the needle electrode into the prostate gland. Failing to do so will result in the failure to create a lesion of sufficient size otherwise required for beneficial results. As with radiofrequency catheter ablation of cardiac tissue, then, the ability to create a lesion of the necessary size to alleviate BPH symptoms is limited and thus requires multiple insertions of the electrode into the prostate.

A typical lesion created with a dry electrode using RF current and a single insertion will normally not exceed one centimeter in diameter. This small size—often too small to be of much or any therapeutic benefit—stems from the fact that the tissue surrounding the needle electrode tends to desiccate as the temperature of the tissue increases, leading to the creation of a high resistance to the further passage of current from the needle electrode into the tissue, all as previously noted with regard to the formation of coagulum on an electrosurgical scalpel. This high resistance-more properly termed impedance since typically an alternating current is being used—between the needle electrode and the base electrode is commonly measured by the RF current generator. When the measured impedance reaches a pre-determined level, some prior art generators will discontinue current generation. Discontinuance of the ablation procedure under these circumstances is necessary to avoid injury to the patient.

Thus, a typical procedure with a dry electrode may involve placing the needle electrode at a first desired location; energizing the electrode to ablate the tissue; continue applying current until the generator measures a high impedance and shuts down; moving the needle to a new location closely adjacent to the first location; and applying current again to the tissue through the needle electrode. This cycle of electrode placement, electrode energization, generator shut down, electrode re-emplacement, and electrode re-energization, will be continued until a lesion of the desired size has been created. As noted, this increases the length of the procedure for the patient. Additionally, multiple insertions increases the risk of at least one of the placements being in the wrong location and, consequently, the risk that healthy tissue may be undesirably affected while diseased tissue may be left untreated. The traditional RF ablation procedure of using a dry ablation therefore includes several patient risk factors that both patient and physician would prefer to reduce or eliminate.

The therapeutic advantages of RF current could be increased if a larger lesion could be created safely with a single positioning of the current-supplying electrode. A single positioning would allow the procedure to be carried out more expeditiously and more efficiently, reducing the time involved in the procedure. Larger lesions can be created in at least two ways. First, simply continuing to apply current to the patient with sufficiently increasing voltage to overcome the impedance rises will create a larger lesion, though almost always with undesirable results to the patient. Second, a larger lesion can be created if the current density, that is, the applied electrical energy, could be spread more efficiently throughout a larger volume of tissue. Spreading the current density over a larger tissue volume would correspondingly cause a larger volume of tissue to heat in the first instance. That is, by spreading the applied power throughout a larger tissue volume, the tissue would heat more uniformly over a larger volume, which would help to reduce the likelihood of generator shutdown due to high impedance conditions. The applied power, then, will cause the larger volume of tissue to be ablated safely, efficiently, and quickly.

Research conducted under the auspices of the assignee of the present invention has focused on spreading the current density throughout a larger tissue volume through the creation, maintenance, and control of a "virtual electrode" within or adjacent to the tissue to be ablated. A virtual electrode can be created by the introduction of a conductive fluid, such as isotonic or hypertonic saline, into or onto the tissue to be ablated. The conductive fluid will facilitate the spread of the current density substantially equally throughout the extent of the flow of the conductive fluid, thus creating an electrode—a virtual electrode—substantially equal in extent to the size of the delivered conductive fluid. RF current can then be passed through the virtual electrode into the tissue.

A virtual electrode can be substantially larger in volume than the needle tip electrode typically used in RF interstitial ablation procedures and thus can create a larger lesion than can a dry, needle tip electrode. That is, the virtual electrode spreads or conducts the RF current density outward from the RF current source—such as a current carrying needle, forceps or other current delivery device—into or onto a larger volume of tissue than is possible with instruments that rely on the use of a dry electrode. Stated otherwise, the creation of the virtual electrode enables the current to flow with reduced resistance or impedance throughout a larger volume of tissue, thus spreading the resistive heating created by the current flow through a larger volume of tissue and thereby creating a larger lesion than could otherwise be created with a dry electrode.

While the efficacy of RF current ablation techniques using a virtual electrode has been demonstrated in several studies, the currently available instruments useful in such procedures lags behind the research into and development of hoped-for useful treatment modalities for the ablation of soft tissue and malignancies.

It would be desirable to have an apparatus capable of creating a virtual electrode for the controlled application of tissue ablating RF electric current to a tissue of interest so as to produce a lesion of desired size and configuration.

SUMMARY OF THE INVENTION

One aspect of the present invention provides a surgical apparatus for delivering conductive fluid to a target site for subsequent formation of a virtual electrode to ablate bodily tissue at the target site by applying a current to the delivered conductive fluid. The surgical apparatus comprises an elongated device forming a helical needle assembly. The helical needle assembly includes a helical needle configured to engage bodily tissue. The helical needle is hollow for delivering conductive fluid from a fluid source and forms a needle tip. In one preferred embodiment, an electrode is associated with the helical needle assembly for applying a current to conductive fluid delivered from the helical needle assembly. During use, the helical needle assembly is maneuvered into contact with bodily tissue at a desired location. Conductive fluid is delivered to the tissue via the hollow helical needle. The electrode applies a current to the so-delivered conductive fluid, thereby creating a virtual electrode for ablating the bodily tissue.

Another aspect of the present invention relates to a surgical system for creating a virtual electrode to ablate bodily tissue. The system includes a fluid source, a current source and a surgical instrument. The fluid source maintains a supply of conductive fluid. The current source is configured to selectively supply a current. Finally, the surgical instrument includes an elongated device forming a helical needle and an electrode associated with the helical needle. The helical needle is configured to engage bodily tissue. Further, the helical needle is hollow and is fluidly connected to the fluid source for delivering the conductive fluid. Finally, the helical needle terminates in a needle tip. The electrode is associated with the helical needle and is connected to the current source. With this configuration, during use, the helical needle is maneuvered into engagement with a desired location of bodily tissue. Conductive fluid is delivered to the bodily tissue via the helical needle. The current source is then activated to supply a current to the electrode, in turn applying a current to the conductive fluid delivered from the helical needle. Application of the current to the delivered conductive fluid creates a virtual electrode, thereby ablating bodily tissue in contact therewith.

DETAILED DESCRIPTION OF THE PRESENT INVENTION

Figure 1:
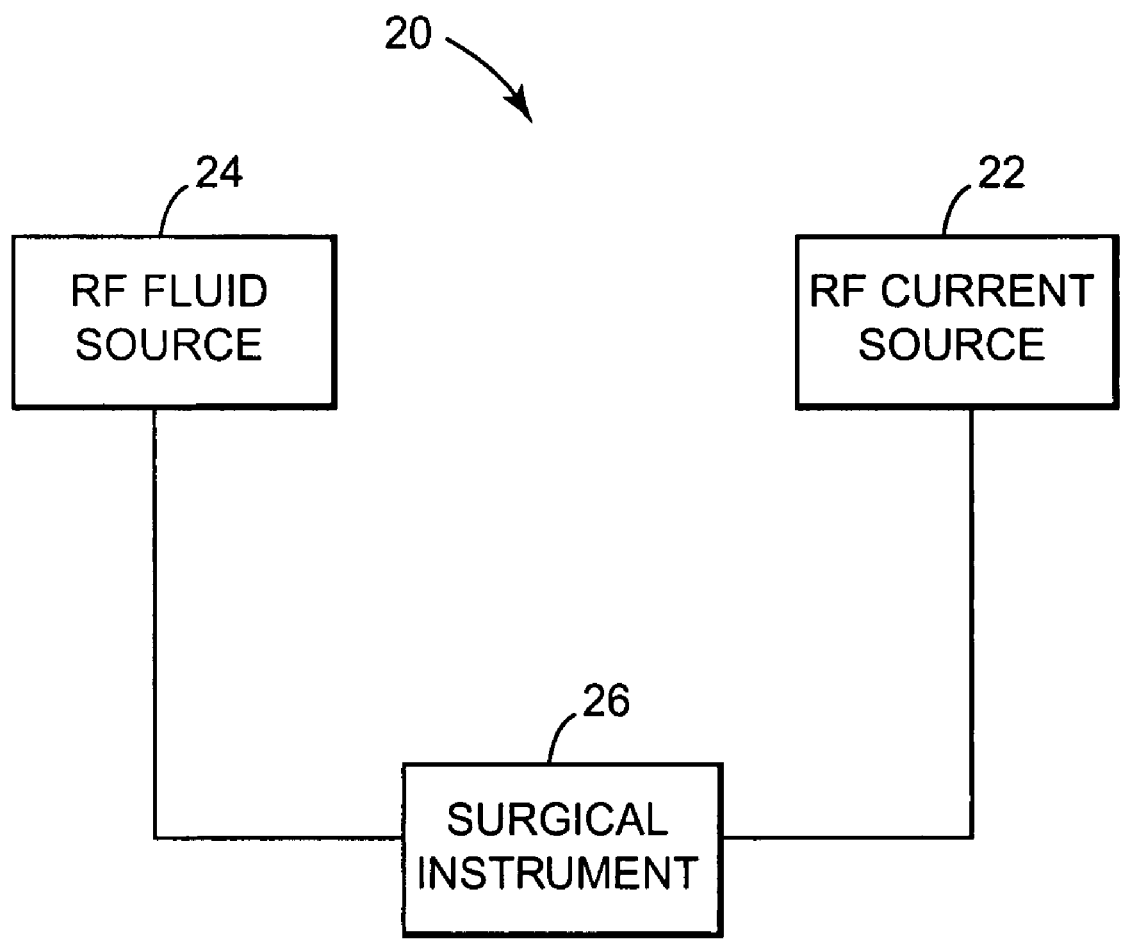
FIG. 1 is a block diagram of a surgical system for creating a virtual electrode to ablate bodily tissue in accordance with the present invention.

FIG. 1 illustrates in block form a surgical system 20 for RF ablation useful with the present invention. The surgical system 20 includes a current source of radiofrequency alternating electric current 22, a fluid source of RF ablating fluid 24, including but not limited to saline and other conductive solutions, and a surgical instrument 26 for delivering the RF current and the ablation fluid to a tissue site (not shown) for ablation purposes. In one preferred embodiment, the surgical instrument 26 is connected to the current source 22 and the fluid source 24. It will be understood that the current source 22 and the fluid source 24 may be combined into a single operational structure controlled by an appropriate microprocessor for a controlled delivery of ablating fluid and a controlled application of RF current, both based upon measured parameters such as but not limited to, flow rate, tissue temperature at the ablation site and at areas surrounding the ablation site, impedance, the rate of change of the impedance, the detection of arcing between the surgical instrument and the tissue, the time period during which the ablation procedure has been operating, and additional factors as desired.

While the surgical instrument 26 is shown as being connected to both the current source 22 and the fluid source 24, the present system is not so limited but could include separate instruments for those purposes. For example, a separate needle or similar apparatus could be used to deliver the current and a separate needle or needles could be used to deliver fluid to the target tissue. In addition, the application of the surgical system 20 illustrated in FIG. 1 is not limited to the use of straight needles or helical needles as surgical instruments but could find use with any type of instrument wherein a conductive solution is delivered to a tissue and an RF current is applied to the tissue through the conductive fluid. Such instruments thus would include straight needles, helical needles, forceps, roller balls, or other instruments for the treatment of vascular disorders, and any other instrument.

Figure 2:
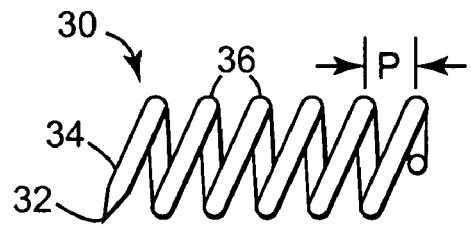
FIG. 2 is an enlarged, side view of a helical needle portion of a surgical instrument used with the system of FIG. 1.

As described above, the surgical instrument 26 may assume a wide variety of forms. In accordance with the present invention, however, the surgical instrument includes an elongated device terminating in a helical needle assembly configured to deliver the conductive fluid as well as to apply a current to the so-delivered fluid. Various embodiments of acceptable helical needle configurations are shown in FIGS. 2-15. For example, FIG. 2 illustrates one embodiment of a helical needle or helical needle assembly 30. The helical needle 30 is preferably hollow, terminating in a needle tip 32 at a distal end 34 thereof. The needle tip 32 defines an opening (not shown) for delivering conductive fluid supplied to the helical needle via the fluid source 24 (FIG. 1). Further, as previously described, the helical needle 30 is preferably configured to serve as an electrode for applying a current, via the current source 22 (FIG. 1), to the delivered conductive fluid. With the above in mind, the helical needle defines a pitch P between adjacent coils 36 that increases in the distal direction. This varying pitch facilitates first the engagement of the needle tip 32 with tissue (not shown) at a target site and its initial threading therein. As the pitch between adjacent coils 36 of the helical needle 30 decreases in the proximal direction, the adjacent coils 36 more tightly engage the tissue, thereby providing a better seal between the tissue and the needle coils 36. This greater sealing ability reduces the likelihood that the conductive fluid, which is heated during the ablation process to a temperature capable of killing cells, will not leak back along the track in the tissue made by the helical needle 30. Thus, the conductive solution will tend to stay closely adjacent to the needle tip 32 rather than leak backwards along the needle track and unintentionally and undesirably damage or destroy other healthy tissue.

Figure 3:
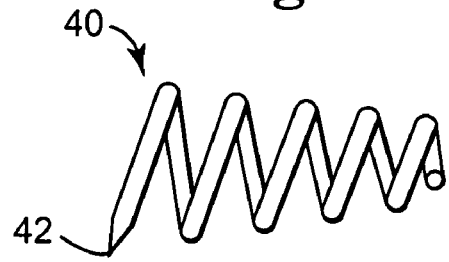
FIG. 3 is a side view of an alternative helical needle in accordance with the present invention.
Figure 4:
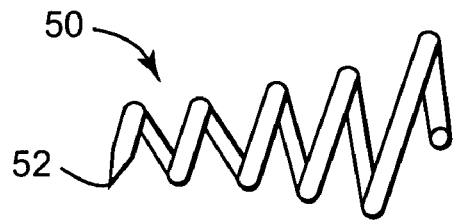
FIG. 4 is an enlarged, side view of an alternative helical needle in accordance with the present invention.

Referring now to FIGS. 3 and 4, alternative embodiments of a fluid and RF current delivery helical needle 40 and 50 are illustrated. Both helical needles 40 and 50 are hollow, terminating in a needle tip 42, 52, respectively, and have a variable diameter that changes in the proximal to distal direction. In the case of the helical needle 40, an outer diameter of the helical needle 40 increases in the proximal to distal direction, whereas with the helical needle 50, the outer diameter decreases in the proximal to distal direction. Varying the diameter in this manner may allow for better sealing of the tissue (not shown) in the affected region against the coils comprising the respective helical needle 40 or 50. That is, alternating the diameter in the manner shown increases the loading of the tissue across the various coils unlike a uniformly coiled needle, wherein the tissue loading is uniform across the coils. Varying the diameter will also affect the amount of torque that must be applied by a surgeon to screw the needle tip 42, 52 into the tissue to be ablated. Thus, with respect to the helical needle 40, as the helical needle 40 is turned into the tissue, the torque necessary to rotate the needle tip 42 increases because the coils force the engaged tissue into a smaller diameter, thus substantially sealing a resulting needle track against leakage of heated conductive fluid there along. Similarly, with respect to the helical needle 50 as shown in FIG. 4, the helical needle 50 first engages a relatively small portion of tissue and subsequently forces the larger diameter coils into the same needle track as followed by the initially small diameter needle tip 52.

Figure 5:
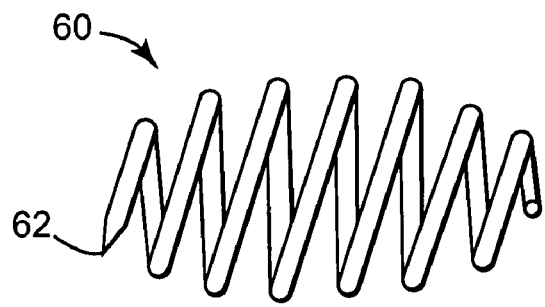
FIG. 5 is an enlarged, side view of an alternative helical needle in accordance with the present invention.

Referring now to FIG. 5, an alternate embodiment of helical needle 60 useful in an RF ablation procedure is shown. As with previous embodiments, the helical needle 60 is hollow to provide a flow path for conductive fluid, and defines a needle tip 62 through which the conductive fluid exits the helical needle 60. Additionally, the helical needle 60 has a diameter that first increases in the proximal to distal direction and then decreases to a diameter somewhat similar to the initial coil diameter at the needle tip 62.

Figure 6:
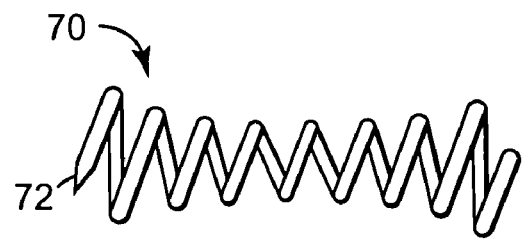
FIG. 6 is an enlarged, side view of an alternative helical needle in accordance with the present invention.

Yet another alternative embodiment of a helical needle 70 is shown in FIG. 6. The helical needle 70 has a coil diameter that decreases in the proximal to distal direction for a predefined predetermined distance and then increases to a diameter substantially equal to the original diameter. Once again, the helical needle 70 is hollow and has a needle tip 72 defining an opening for the outflow of conductive fluid. Both of the embodiments 60 and 70 shown in FIGS. 5 and 6 provide for a varying torque and increased sealing ability due to the action of the helical needle 60 and 70 forcing the tissue (not shown) to follow the coils through the tissue as the diameter thereof varies.

Figure 7:
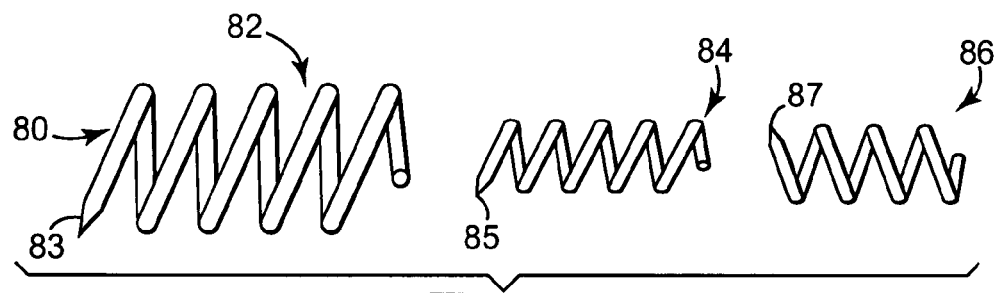
FIG. 7 is an enlarged, exploded view of an alternative helical needle assembly in accordance with the present invention.

Yet another alternate embodiment of a helical needle assembly 80 is shown in exploded view in FIG. 7. The helical needle assembly 80 comprises a plurality of concentric helical needles 82, 84 and 86. Alternatively, only two such helical needles could be provided or additional helical needles may be used as desired. The use of a plurality of concentrically disposed helical needles 82, 84 and 86 allows the physician to engage thinner tissues (not shown), such as the atrial wall. The concentric helical needles 82, 84 and 86 are preferably wound in the same direction to facilitate insertion and capture of the tissue. Each helical needle 82, 84 and 86 includes a needle tip 83, 85 and 87, respectively. As desired, the helical needles 82, 84 and 86 are hollow to provide a fluid path for conductive fluid from the fluid source 24 (FIG. 1) with the fluid exiting through needle tips 83, 85 and 87 respectively. That is, one or more of the helical needles 82, 84 or 86 could be used to provide fluid to the tissue to be ablated. Additionally, one or more of the helical needles 82, 84 or 86 may be used as a suction path for removal of conductive fluid.

Figure 8:
FIG. 8 is an enlarged, side view of an alternative helical needle assembly in accordance with the present invention.

Yet another alternative embodiment of a helical needle assembly 90 is depicted in FIG. 8. In general terms, the helical needle assembly 90 comprises a plurality of helical needles, here 92 and 94, wound parallel to one another. As with previous embodiments, each of the helical needles 92 and 94 are preferably hollow, terminating in an open, needle tip 96 and 98, respectively. The use of a parallel assembly would enable the physician performing an ablation procedure to use one of the helical needles 92 or 94 as a fluid path for providing conductive fluid from the fluid source 24 (FIG. 1) to the tissue (not shown) to be ablated and the second helical needle 92 or 94 as a vacuum source for removal of the conductive fluid. The use of suction to remove the ablation fluid either during or at the end of the procedure will reduce the likelihood of leakage of the hot conductive fluid backwards along the needle track.

Figure 9:
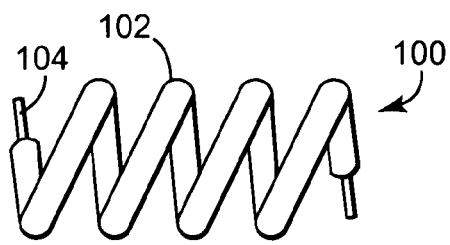
FIG. 9 is an enlarged, side view of an alternative helical needle assembly in accordance with the present invention.

Yet another alternative embodiment of a helical needle assembly 100 is shown in FIG. 9. The helical needle assembly 100 is similar to the helical needle assembly 80 (FIG. 7) previously described. The helical needle assembly 100 includes outer and inner helical needles 102 and 104 concentrically arranged. As with the embodiment shown in FIG. 7, the concentric helical needles 102, 104 may be used to deliver fluid at different depths in a tissue (not shown) or one or more flow paths could be used to provide suction and removal of the ablating solution from the tissue during or subsequent to the termination of the application of RF power to the tissue, via the current source 22 (FIG. 1). As shown in FIG. 9, only two such concentric helical needles 102, 104 are shown, though multiple coils in excess of two could be used.

It will be understood that the various configurations could be combined in several of the embodiments shown. For example, the variable pitch shown in FIG. 2 could be combined with the variable diameters shown in FIGS. 3-5 and 8.

In addition, the variable diameter structure shown in FIGS. 3-6 could be combined with the parallel assembly construction shown in FIG. 8.

Figure 10:
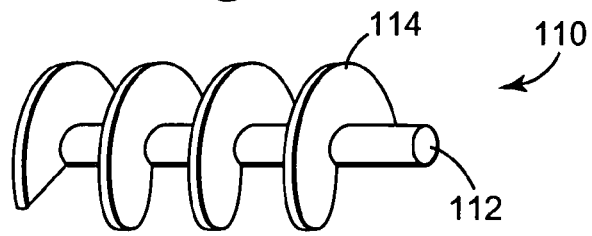
FIG. 10 is an enlarged, perspective view of an alternative helical needle in accordance with the present invention.
Figure 11:
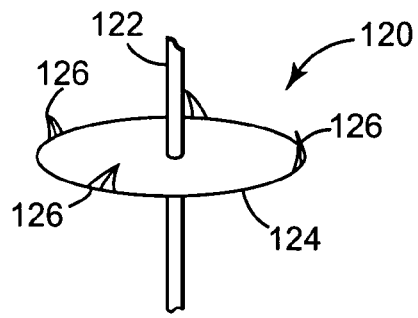
FIG. 11 is an enlarged, perspective view of an alternative helical needle assembly in accordance with the present invention.

Referring now to FIGS. 10 and 11, alternate embodiments of helical needle assemblies 110 and 120, including alternate means of anchoring a needle to a tissue (not shown), are shown. With reference to FIG. 10, the helical needle assembly 110 is an archimedes type screw comprising a central shaft 112 about which a helical flight 114 is wound. The central shaft 112 is preferably hollow for delivering conductive fluid from the fluid source 24 (FIG. 1). The helical needle assembly 120 has a substantially straight fluid and current delivery portion 122 mounted substantially centrally of a disc 124 having a plurality of starting threads 126. The starting threads 126 will engage the tissue (not shown), such as a cardiac wall, and will anchor the helical needle assembly 120 thereto. Though it be understood that the straight needle portion 122 would penetrate the tissue wall to deliver fluid and electric current from the fluid source 24 (FIG. 1) and the current source 22 (FIG. 1), respectively.

Figure 12:
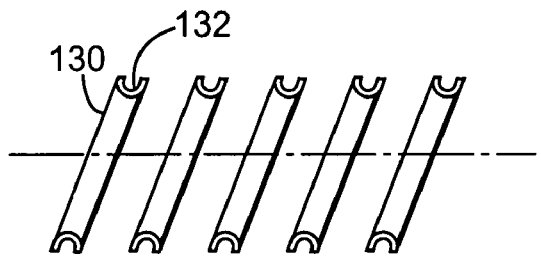
FIG. 12 is an enlarged, cross-sectional view of an alternative helical needle in accordance with the present invention.
Figure 13:
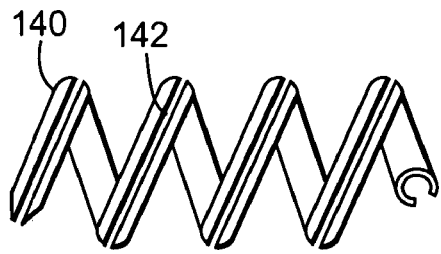
FIG. 13 is an enlarged, side view of an alternative helical needle in accordance with the present invention.
Figure 14:
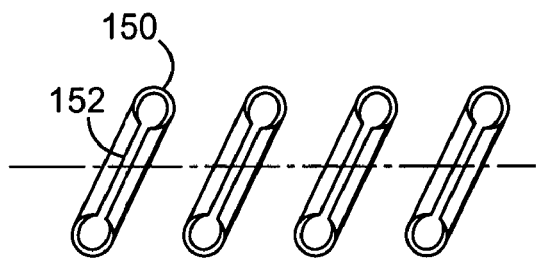
FIG. 14 is an enlarged, cross-sectional view of an alternative helical needle in accordance with the present invention.

In the discussion of FIGS. 2-11, it has been understood that each embodiment described would deliver conductive fluid through a single aperture at the needle tip. The present invention is not so limited however. Thus, the fluid could be delivered to the tissue (not shown) by laser drilling a plurality of holes along the length of the various coiled needle configurations. These laser drilled fluid delivery apertures could be configured as desired in terms of size and well as number and distance from each other along the longitudinal extent of the helical needle. FIGS. 12-14 illustrate yet additional fluid delivery methods. Thus, as shown at FIG. 12, a helical needle 130 could include openings 132 extending along part of an outer diameter of the helical needle 130. Alternatively, a helical needle 140 is shown in FIG. 13 as including an open slit 142 extending along an outer diameter thereof. Conversely, a helical needle 150 is depicted in FIG. 14 as having a coil structure wherein a fluid delivery aperture or slit 152 extends along the inner diameter of the needle coils.

Figure 15:
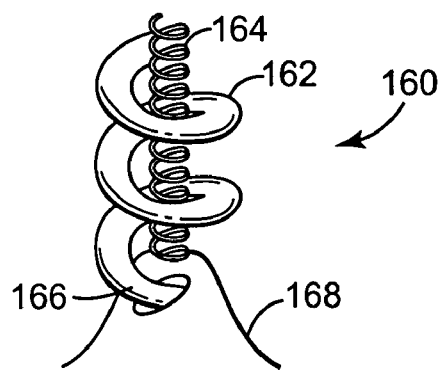
FIG. 15 is an enlarged, perspective view of an alternative helical needle assembly in accordance with the present invention.

FIG. 15 illustrates yet another alternative embodiment of a helical needle assembly 160 in accordance with the present invention including a pair of concentric helical needles 162 and 164. The first helical needle 162 is a large diameter needle whose end 166 (shown partially) is used to anchor the instrument in tissue 168. The second helical needle 164 has a smaller diameter than the first helical needle 162 and is disposed substantially coaxially therewith. Each of the helical needles 162 and 164 may include a hollow interior to provide a flow path for conductive fluid from the fluid source 24 (FIG. 1) and each could be electrically active, via the current source 22 (FIG. 1), through known appropriate connections. Either or both of the helical needles 162, 164 may be used to deliver conductive fluid and either of the helical needles 162, 164 could be electrically active. Alternatively, the helical needles 162 and 164 could form a bipolar needle wherein the helical needles 162, 164 have opposing polarities and the current provided by one travels to the other.

Although the present invention has been described with reference to preferred embodiments, workers skilled in the art will recognize that changes may be made in form and detail without departing from the spirit and scope of the invention.

What is claimed is:

1. A medical procedure comprising:
   providing a medical device comprising first and second helical coils configured to engage bodily tissue, the first and second helical coils comprising at least one opening for delivery of a conductive fluid to a tissue treatment site, the first and second helical coils wound parallel to one another, the first and second helical coils configured to apply electric current to bodily tissue, the first helical coil serving as a first electrode of a bipolar electrode configuration and the second helical coil serving as the second electrode of the bipolar electrode configuration;
   maneuvering the first and second helical coils into contact with tissue;
   delivering the conductive fluid to the tissue; and
   applying electric current to the tissue.

2. The medical procedure according to claim 1 wherein the first coil comprises a plurality of conductive fluid delivery openings.

3. The medical procedure according to claim 2 wherein the plurality of conductive fluid delivery openings are located along the length of the first coil.

4. The medical procedure according to claim 1 wherein the conductive fluid delivery opening of the first coil comprises a hole.

5. The medical procedure according to claim 1 wherein the conductive fluid delivery opening of the first coil comprises a slit.

6. The medical procedure according to claim 1 wherein the second coil comprises a plurality of conductive fluid delivery openings.

7. The medical procedure according to claim 6 wherein the plurality of conductive fluid delivery openings are located along the length of the second coil.

8. The medical procedure according to claim 1 wherein the conductive fluid delivery opening of the second coil comprises a hole.

9. The medical procedure according to claim 1 wherein the conductive fluid delivery opening of the second coil comprises a slit.

10. The medical procedure according to claim 1 wherein the first coil is provided by a first needle and the second coil is provided by a second needle.

11. The medical procedure according to claim 10 wherein the first needle is hollow and the second needle is hollow.

12. A medical procedure comprising:
    providing a medical device comprising first and second helical coils configured to engage bodily tissue, the first and second helical coils comprising at least one opening for delivery of a conductive fluid to a tissue treatment site, the second helical coil concentrically disposed within the first helical coil, the first and second helical coils configured to apply electric current to bodily tissue, the first helical coil serving as a first electrode of a bipolar electrode configuration and the second helical coil serving as the second electrode of the bipolar electrode configuration;
    maneuvering the first and second helical coils into contact with tissue;
    delivering the conductive fluid to the tissue; and
    applying electric current to the tissue.

13. The medical procedure according to claim 12 wherein the first coil comprises a plurality of conductive fluid delivery openings.

14. The medical procedure according to claim 13 wherein the plurality of conductive fluid delivery openings are located along the length of the first coil.

15. The medical procedure according to claim 12 wherein the conductive fluid delivery opening of the first coil comprises a hole.

16. The medical procedure according to claim 12 wherein the conductive fluid delivery opening of the second coil comprises a slit.

17. The medical procedure according to claim 12 wherein the second coil comprises a plurality of conductive fluid delivery openings.

18. The medical procedure according to claim 17 wherein the plurality of conductive fluid delivery openings are located along the length of the second coil.

19. The medical procedure according to claim 12 wherein the conductive fluid delivery opening of the second coil comprises a hole.

20. The medical procedure according to claim 12 wherein the conductive fluid delivery opening of the second coil comprises a slit.

21. The medical procedure according to claim 12 wherein the first coil is provided by a first needle and the second coil is provided by a second needle.

22. The medical procedure according to claim 21 wherein the first needle is hollow and the second needle is hollow.

23. The medical procedure according to claim 12 wherein the second coil has an outer diameter less than an inner diameter defined by the first coil.

* * * * *